United States Patent [19]

Watmough et al.

[11] Patent Number: 4,735,604
[45] Date of Patent: Apr. 5, 1988

[54] APPARATUS FOR REMOVING BIOLOGICAL MATERIAL

[75] Inventors: David J. Watmough; Kwan Chan; D. Terence Hope; Keith Moir, all of Aberdeen, Scotland

[73] Assignee: The University Court of The University of Aberdeen, Aberdeen, Scotland

[21] Appl. No.: 852,173

[22] Filed: Apr. 15, 1986

[30] Foreign Application Priority Data

Apr. 16, 1985 [GB] United Kingdom ............... 8509664

[51] Int. Cl.$^4$ ............................................. A61B 17/20
[52] U.S. Cl. ........................................ 604/22; 604/35; 128/305; 128/303.1; 128/317
[58] Field of Search .................. 604/22, 35; 128/305, 128/317, 329 R, 755, 303.1, 24 A; 433/118, 122; 30/123.3, 272

[56] References Cited

U.S. PATENT DOCUMENTS

| | | | |
|---|---|---|---|
| 1,948,109 | 2/1934 | Hager | 128/318 |
| 2,070,281 | 2/1937 | Leggiadro | 128/305 |
| 2,227,727 | 1/1941 | Leggiadro | 30/272 R |
| 3,012,322 | 12/1961 | Thompson | 604/35 |
| 3,642,002 | 2/1972 | Otterstrom | 128/303 R |
| 3,809,093 | 5/1974 | Abraham | 128/305 |
| 3,905,105 | 9/1975 | Tuke | 128/317 |
| 3,913,582 | 10/1975 | Sharon | 128/303.1 |
| 4,016,882 | 4/1977 | Broadwin et al. | 128/305 |
| 4,246,902 | 1/1981 | Martinez | 604/22 |
| 4,314,560 | 2/1982 | Helfgott et al. | 604/35 |
| 4,428,748 | 1/1984 | Peyman et al. | 128/305 |
| 4,542,741 | 9/1985 | Burgin | 128/305 |

*Primary Examiner*—C. Fred Rosenbaum
*Assistant Examiner*—Mario Constantino
*Attorney, Agent, or Firm*—Birch, Stewart, Kolasch & Birch

[57] ABSTRACT

Apparatus for removing biological material from a body thereof comprising a hollow tubular elongate member, one end of which can engage biological material to be removed, a casing in which a portion of the tubular member is mounted for longitudinal sliding movement, a motor which is connected to the casting and has a rotatable drive shaft, means for coupling the rotation of the drive shaft to the tubular member so as longitudinally to vibrate the tubular member and means for withdrawing removed biological material up the tubular member from the said end thereof.

14 Claims, 3 Drawing Sheets

APPARATUS FOR REMOVING BIOLOGICAL MATERIAL

BACKGROUND OF THE INVENTION

The present invention relates to an apparatus for removing biological material and in particular to such apparatus which includes means for aspirating the biological material thereby to suck away the removed material from the region of the body being operated upon.

DESCRIPTION OF THE PRIOR ART

A known surgical instrument for breaking up and removing unwanted tissue is disclosed in British patent specification No. 1215881. The surgical instrument disclosed therein employs a magnetostrictive transducer for vibrating the operative tip of the instrument at a resonant frequency of approximately 25 kHz.

The instrument suffers from a number of disadvantages. First, the instrument is operated ultrasonically at a highly tuned resonant frequency. This requires the size and weight of the components of the instrument, and in particular the size and shape of the operative tip, to be precisely controlled to ensure resonance and therefore optimum performance. The instrument is not versatile since it must be of a predetermined length which cannot be varied in practice.

Secondly, the instrument is operated at a very high frequency and this makes the instrument expensive to manufacture due to the high precision required. Also, the high frequency vibrations render the operative tip very liable to wear and tear and any damage to the tip tends to put the instrument off resonance which necessitates replacement of the tip. We have found that the metal tip is particularly prone to cavitation in the region where it impacts the tissues to be removed and that the tip must be either replaced or reconditioned after every operation. This is very expensive, particularly since the high frequency vibrations put great mechanical demands on the material of the tip and so the tip must be made of a high quality metal which is precisely made with the required dimensions.

Third, the instrument is vibrated at its resonant frequency and so the vibrating tip must be rigid. The tip cannot be flexible, which is desirable in particular surgical applications.

SUMMARY OF THE INVENTION

The present invention provides apparatus for removing biological material from a body thereof comprising a hollow tubular elongate member, one end of which can engage biological material to be removed, a casing in which a portion of the tubular member is mounted for longitudinal sliding movement, a motor which is connected to the casing and has a rotatable drive shaft, means for coupling the rotation of the drive shaft to the tubular member so as longitudinally to vibrate the tubular member and means for withdrawing removed biological material up the tubular member from the said end thereof.

DESCRIPTION OF THE PREFERRED EMBODIMENTS

Figure 1:
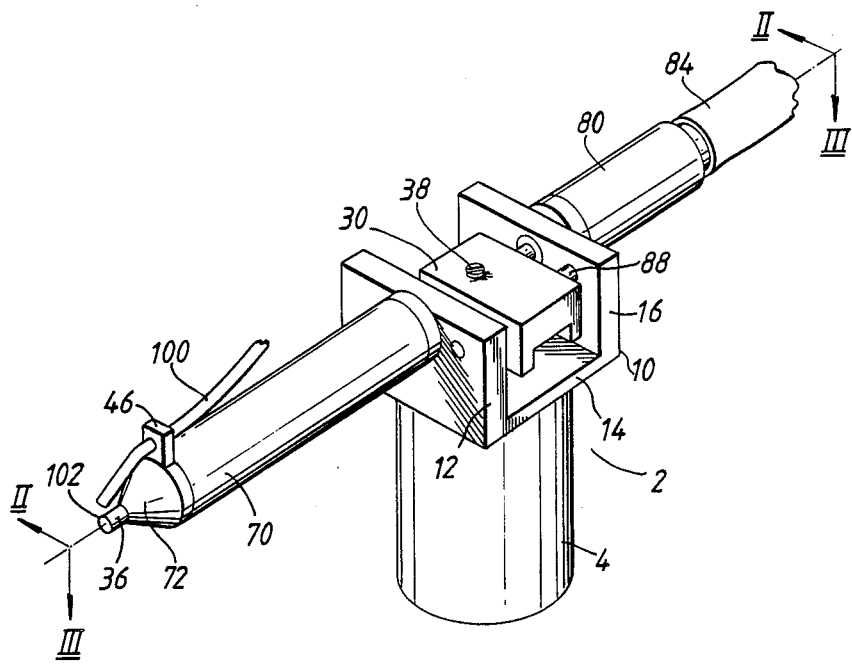
FIG. 1 shows schematically a perspective view of an apparatus for removing biological material in accordance with the present invention.

In the drawings, the particular dimensions of the apparatus are not shown to scale for the sake of clarity of illustration.

Referring to FIGS. 1 to 4, a surgical aspirator 2 includes a housing 4 in which an electic motor 6 is mounted. The motor 6 is preferably a 24 volt direct current motor and is preferably a brushless motor which is sealed so as to reduce the possibility of constituting a safety hazard when the motor is operated in an atmosphere containing a flammable anaesthetic gas. The motor 6 is connected to a suitable source of electric power by connecting leads (not shown). The motor 6 is arranged to have an operating speed of 20,000 revolutions per minute. A drive shaft 8 for the motor 6 protrudes from the housing 4 and through the wall of a casing 10. The casing 10 is shaped as a generally U-shaped channel member with three plane walls 12, 14 16. Preferably, the casing 10 is made of aluminum. The drive shaft 8 passes through the bottom wall 14 from the ouside of the U-shaped casing 10 and extends into the channel. The motor housing 4 is mounted on the outside of the bottom wall 14 in a suitable manner. On a free end of the drive shaft 8 is mounted a drive wheel 20. The drive wheel 20 is eccentrically mounted on the end 18 of the drive shaft 8. In the preferred arrangement, the centre of the drive shaft 8 is offset 1 mm from the centre of the drive wheel 20. When drive shaft 8 rotates on energising the electric motor 6, the drive wheel 20 rotates at the same rotational speed as the electric motor 6 and the outer cylindrical surface of the drive wheel 20 rotates eccentrically in a manner similar to a rotating cam surface. The drive wheel 20 is provided with an integral axially extending lug 22 around which a ball race 24, which preferably has ball bearings 26 of 10 mm diameter, is mounted. The ball bearings 26 may be mounted in an annular cage 28 and can roll against the transverse end surface of the drive wheel and the longitudinal cylindrical surface of the lug 22.

A bearing housing 30 comprises an elongate body having a generally U-shaped channel 32 therein. The cross-section of the channel 32 has substantially the same dimensions as the cross-section of the ball race 24 and the bearing housing 30 is disposed over the ball race 24 so that the ball race 24 is snugly received in the channel 32. The bearing housing 30 so disposed fits between the two upright arms of the U-shaped casing 10. Preferably, the bearing housing 30 is composed of a silver-steel.

The bearing housing 30 is provided with an elongate cylindrical bore 34 therethrough which extends transverse to the axis of rotation of the drive shaft 8. A hollow cylindrical tube 36 is mounted in the bore 34 and protrudes from each end of the bore 34. The tube 36 is made of a strong and tough metal which is suitable for use in surgery. Preferably, the tube 36 is composed of surgical stainless steel. The diameter of the tube 36 is slightly less than that of the bore and the tube 36 is fixed in the bore 34 by a grub screw 38 which is screwed into a threaded hole 40 in the upper surface of the bearing housing 30 and engages the cylindrical surface of the tube 36. The grub screw 38 adjustably fixes the tube 36 firmly in the bearing housing 30. The two side walls 12, 16 of casing 8 are each provided with a respective cylindrical hole 42, 44. A pair of elongate bushes 46, 48 are mounted each in a respective hole 42, 44. Each bush 46, 48 has a respective cylindrical cavity 50, 52 therethrough and each cavity 50, 52 is aligned with the elongate bore 34 in the bearing housing 30 so that the tube 36 passes through the cavities 50, 52. The diameter of each cavity 50, 52 is slightly greater than that of the tube 36 so that the tube 36 can slide freely in the bushes 46, 48. Each bush 46, 48 has an end part 54, 56 which has a cylindrical outer surface which bears against the inner cylindrical surface of the respective hole 42, 44. The other end part 58, 60 of each bush 46, 48 also has a respective cylindrical surface 62, 64 and the two end parts of each bush 46, 48 are separated by a respective outwardly-directed cylindrical flange 66, 68. Preferably, each bush 46, 48 is composed of brass.

One end of a tubular sleeve 70, which may be composed of perspex, is mounted on the cylindrical surface 62 of one of the bushes 46. The sleeve 70 surrounds the tube 36. At the other end of sleeve 70 an end bush 72 is mounted. The end bush 72 has an elongate cylindrical cavity 74 through which the tube 36 extends. One end 76 of the end bush 72 is cylindrical and is pushed into the end of the sleeve 70 and the other end 78 of the end bush 72 is conically tapered and has the tube 36 protruding therefrom through the cylindrical cavity 74 which exits at the point of the cone. The elongate cylindrical cavity 74 in the end bush 72 has a diameter which is slightly greater than that of the tube 36 so that the tube 36 can slide freely in the elongate cylindrical cavity 74. Preferably, the end bush 72 is composed of a material having a low coefficient of sliding friction, such as polytetrafluoroethylene (ptfe), so as to facilitate relative sliding movement between the tube 36 and the end bush 72.

One end of a second sleeve 80, which may also be composed of perspex, is mounted on the cylindrical surface 64 of the other bush 48. The second sleeve 80 has at its other end a connection 82 for a flexible hose 84. In use, the hose 84 is connected to a suction pump. The tube 36 extends into the cylindrical chamber 86 which is defined within the second sleeve 80.

A cylindrical bar 88 extends parallel to the tube 36 through a second elongate bore 90 within the bearing housing 30. The diameter of the bore 90 is greater than that of the bar 88 so that the bearing housing 30 can slide freely along the bar 88. The two ends of the bar 88 are fixed in respective mounting holes 92, 94 in the side walls 12, 16 in the casing 10. Preferably, the bar 88 is composed of stainless steel.

The casing 10 and the exposed moving parts within the casing 10 may be covered by an appropriate cover (not shown).

The end bush 72 is provided with an integral protrusion 96 which has a hole 98 therethrough for receiving and gripping a conduit 100 for delivering liquid from a reservoir (not shown) to the region of the tip 102 of the tube 36.

The tip 102 of the tube 36 may be employed to remove living tissue from a body, for example in surgery, particularly neurosurgery, in a manner which will now be described.

In operation, the electric motor 6 is switched on and rotates the drive shaft 8 and the drive wheel 20 connected thereto at an operating speed of around 20,000 rpm. The lug 22 also rotates eccentrically and causes eccentric rotation of ball race 24. The ball race 24 mounted on drive wheel 20 acts as a cam which transmits the eccentric rotation of the drive wheel 20 to the bearing housing 30 which acts as a cam follower. The bearing housing 30 is restrained from rotational movement by bar 88 on which it is mounted for sliding movement therealong. The eccentric rotation of the drive wheel 20 is thus converted into a translational oscillatory movement of the bearing housing 30. Since tube 36 is fixed in the bearing housing 30 by grub screw 38, the tube 36 also oscillates back and forth along the axis of the surgical aspirator by being slid in bushes 46, 48 and end bush 72. The sleeve 70 and end bush 72 act to hold the vibrating tube 36 straight and reduce any lateral movement of the tube as it is oscillating back and forth.

The vibrating frequency of the tip 102 is around 300 Hz when the electric motor 6 rotates at around 20,000 rpm. The amplitude of vibration of the tip 102 is 1 mm when the axis of the drive shaft 8 is off-set 1 mm from the centre of the drive wheel 20.

When the annular edge of vibrating tip 102 is applied to a body of tissues, the edge can chop through the tissues in each forward oscillatory movement to remove a small sliver of the tissues.

We have found that the effectiveness of the aspirator 2 in chopping through tissue is substantially independent of the frequency of vibration of the tip. The tip may be vibrated at frequencies up to 50 KHz. Also, the amplitude of vibration of the tip may be less than 1 mm.

If desired, the shape and dimensions of the tip 102 may be varied to give optimal tissue removal for a particular application. The tip 102 can be slightly tapered towards its end so that the area of the annular chopping edge is reduced whereby the annular chopping edge impinges with a greater pressure on the tissues. The chopping edge is not sharp enough to cut but rather chops the tissues. Typically, the tube 36 in the region of the tip 102 has an outer diameter of 3 mm and the tubular wall thickness is 0.2 mm. The wall thickness may be varied above and below that value.

The surgical aspirator 2 is also provided with an aspiration system to remove tissue fragments, liquid and other material from the region of the tissues being operated upon. At the same time as the tube 36 is vibrated, a vacuum, typically suction pressure of from 20 to 60 cm of mercury, is applied to cylindrical chamber 86 which causes the tissues, and any loose matter which is in the immediate vicinity of the tip 102, to be sucked up the tube 36 and through hose 84 into a suitable storage facility.

The surgical aspirator 2 is further provided with an irrigation system to provide in the region of the tissues being operated upon a sterile solution for cleaning the surgical field and assisting in the removal of tissue fragments. Sterile saline solution is delivered from conduit 100 to the vibrating tip 102. In an alternative construction, the conduit 100 can be fixed in a corresponding port in the sleeve 70 so that saline solution can be fed between the tube 36 and the sleeve 70. The end bush 72 would be appropriately shaped (e.g. by providing holes therein) to permit the saline solution to flow out of the sleeve 70 and onto the vibrating tip 102. The rate of delivery of the saline solution may be varied as desired. It has been found that increase of the rate of the saline solution which drips into the wound can aid emulsification of the matter being removed from the tissues. This helps the removed tissues to be broken down and thus increases the removal rate of the tissues.

In another arrangement, there may be provided at the tip end of the aspirator 2 a high power water jet for spraying water into the area of tissues being operated upon and cleaning the tissue field of blood and debris.

The surgical aspirator may also be arranged to act as a coagulator for coagulating blood in the region of the tissues being operated upon. In many surgical treatments, it is very advantageous to provide rapid coagulation of blood. To provide coagulation, the metal tube 36 is connected to a source of radio frequency electromagnetic radiation or to another suitable electromagnetic heating system. The tube 36 then acts as an electrode for providing electrocoagulation and cuterization by high frequency diathermic heating of the tissues. In order to provide additional diathermic heating, if desired a coil of wire may be located near the tip 102 of the aspirator 2 for generating eddy currents for heating the tissues.

In a particularly preferred arrangement of the surgical aspirator according to the present invention, the tube 36 is not made wholly of metal but rather is of a composite construction so as to render it flexible whereby the vibrating tube 36 can be deflected laterally in operation. This allows the tip 102 to be bent around corners in the body of tissues being operated upon, so that locations may be reached which would be inaccessible with a straight vibrating tube.

Figure 5:
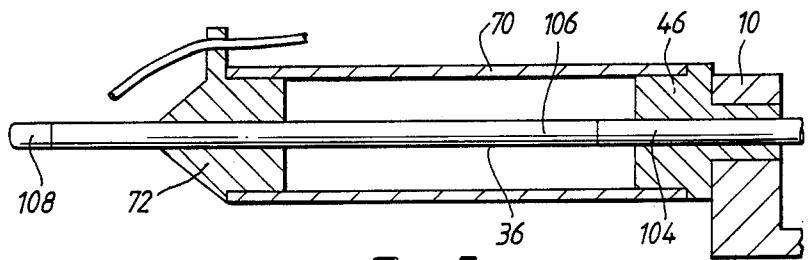
FIG. 5 shows an alternative construction of a vibrating tube for use in the apparatus of FIG. 1.

A suitable flexible tube 36 is shown in FIG. 5. The tube 36 comprises a rigid portion 104 which is fixed to and passes through the bearing housing 30 in the manner described above. The rigid portion 104 may be made of surgical stainless steel. A flexible portion 106 is connected to the end of the rigid portion 104 and extends axially therealong. The flexible portion 106 may be made of a suitable plastics material such as, for example, polyethylene. The flexible portion 106 may be removably attached to the rigid portion 104 so as to allow a number of flexible portions 106 of varying length to be selectively employed. A tip portion 108 is attached to the end of the flexible portion 106. The tip portion 108 is shaped and dimensioned so as to be similar to tip 102 which is shown in FIG. 1. Preferably, the tip portion 108 is removably attached, e.g. by a sliding or screw connection, to the flexible portion 106 so that a number of tip portions 108 can readily be selectively interchanged.

Figure 6:
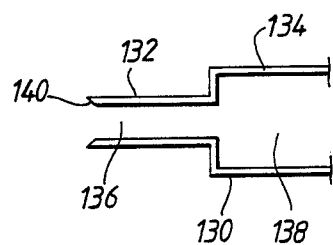
FIG. 6 shows an enlarged longitudinal section through a further alternative construction of the tip of a vibrating tube for use in the apparatus of FIG. 1.
Figure 2:
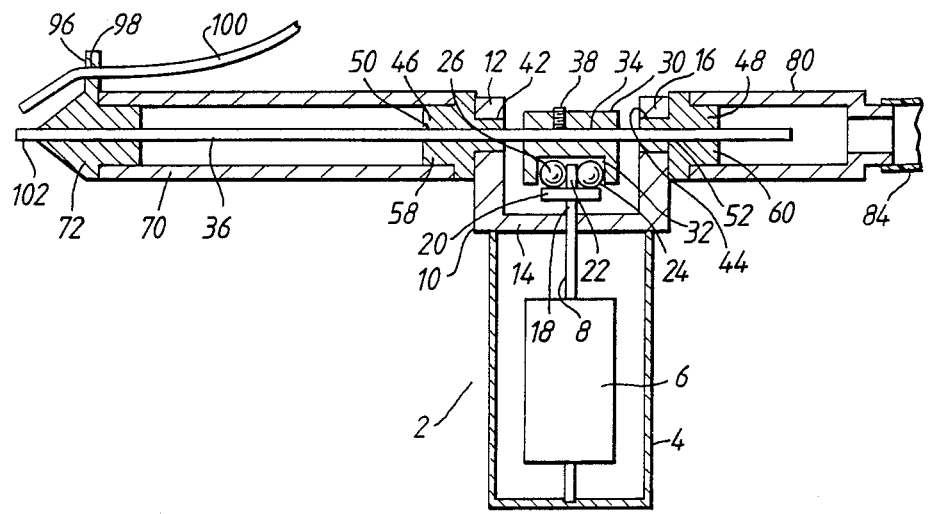
FIG. 2 is a cross-section on line II—II of the apparatus shown in FIG. 1.
Figure 3:
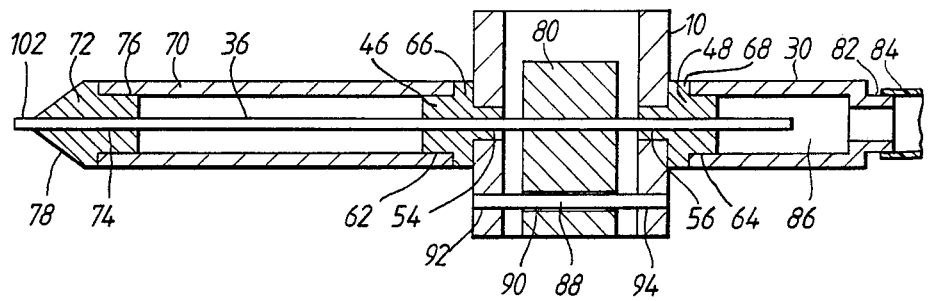
FIG. 3 is a cross-section on line III—III of the apparatus shown in FIG. 1.
Figure 4:
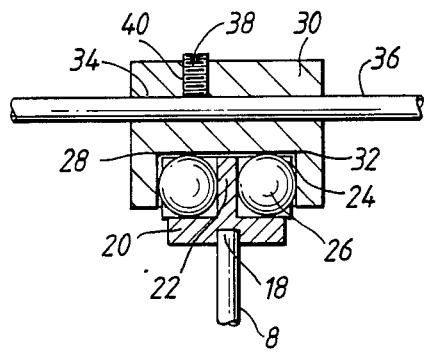
FIG. 4 shows in greater detail the arrangement of the drive means for the apparatus which is shown in FIG. 2.

An alternative construction of the tip of the tube is shown in FIG. 6, which is an enlarged section through the tip of the tube. The tip 130 comprises an end part 132 which is mounted on or integral with the tube 134. The end part 132 is also tubular and is coaxial with the tube 134. The diameter of the end part 132 is less than that of the tube 134 whereby the cross section of the bore 136 through the end part 132 is less than that of the bore 138 of the tube. This tends to increase the suction pressure at the end part which increases the aspiration efficiency of the device. Typically, the outer diameter of the end part 132 is 3 mm, the outer diameter of the tube 134 is 5 to 6 mm and the tubular wall thickness of 0.2 mm. The annular end wall 140 of the end part 132 is tapered radially outwardly to form a cutting edge which facilitates the chopping action on the tissues to be removed. The provision of a tip of reduced diameter also tends to increase the rigidity and stability of the tube.

Referring again to FIG. 5, the composite tube 36 is mounted within sleeve 70, one end of which is attached to the casing 10 by bush 46. End bush 72 is made of a low-friction material such as polytetrafluoridethylene (ptfe) and is mounted at the other end of the sleeve 70. The length of the sleeve 70 can be varied so as to alter the length of the flexible tube 36 which protrudes from the tip end of the sleeve 70 and thereby vary the amount of tube 36 which can be bent by an operator in use. Also, the sleeve 70 may be arranged so as to provide electrocoagulation of blood. When the sleeve 70 is of a plastics material, the outer cylindrical surface thereof is coated with a metallic film which can act as an electrode in a diathermic heating system. Alternatively, the sleeve 70 may be composed of a metal, such as stainless steel, which can act as such an electrode.

In a still further alternative arrangement, the flexible portion 106 of the tube 36 is made of a material which transmits visible light, such as a clear plastics material. A source of visible light, such as the end of one or more optical fibres, is coupled with the flexible portion 106. Light is shone from the optical fibre(s) into the flexible portion 106 which acts as a light guide and delivers light to the region of the vibrating tip 108 of the oscillating tube 36. This provides convenient illumination of the area of tissues being operated upon.

In another development, the tube 36 can act as a light or acoustic wave guide to permit the surgical field to be imaged on a display unit which is positioned at a remote location.

Although the illustrated surgical aspirator 2 incorporates an electric motor 6 to drive the vibrating tip 102, it will be readily understood that other drive means may alternatively may be used. For example, the motor could be a compressed gas motor which has a turbine which is driven by compressed gas from a suitable supply. Alternatively, the motor could employ a piston driven system. If desired, the motor may be coupled to the drive wheel by a magnetic coupling so that there is no direct mechanical coupling between the motor and the drive wheel. Such an arrangement would be very efficient at the high operating speeds of the motor due to the low frictional resistance of the magnetic coupling.

We have found that it is important for the vibration of the tip to be insulated as much as possible from that part of the aspirator 2 which is held by the surgeon in use. Preferably, the various parts of the aspirator are connected together by means of low-vibration transmitting fastening devices, such as nylon screws, which reduce the transmission of vibration to the surgeon's hand.

The surgical aspirator of the present invention has a number of advantages over the known aspirators which employ a magnetostrictive transducer to vibrate the tip at very high frequency. Such known aspirators are vibrated at the resonant frequency of the aspirator and this requires the dimensions of the components in the aspirator to be set precisely in order that the aspirator can be tuned to its resonant frequency for optimal performance.

Since in the present invention the tip is vibrated at a relatively low frequency in a non-resonant manner, the size of the components of the aspirator, and in particular the length and thickness of the tube, can be varied as desired without affecting the performance of the aspirator. This is very important since it greatly increases the versatility of the aspirator by permitting a variety of tips, and also of lengths of the vibrating tube, to be used so that the aspirator can be employed in many different applications.

Furthermore, the aspirator of the present invention can have a flexible vibrating tube which permits the tip to access locations in the tissues which could not be reached with a straight rigid tube. The known aspirators cannot be provided with such a flexible tube since they operate at a resonant frequency and so the tube is necessarily rigid.

In addition, since the aspirator of the present invention can be operated at relatively low vibration frequencies, the damage which results to the tip is far less than the damage which occurs to the tip in the known ultrasonically vibrated aspirators. Also, in the known altrasoncially vibrated aspirators it is crucial for the end of the tip not to be damaged or deformed as this very easily causes the vibration to go off resonance. In the present invention however, such damage can be more easily accomodated since the tip is vibrated in a non-resonant manner. When replaceable tips are used, the damaged tips can readily be replaced without replacing the whole tube.

Figure 7:
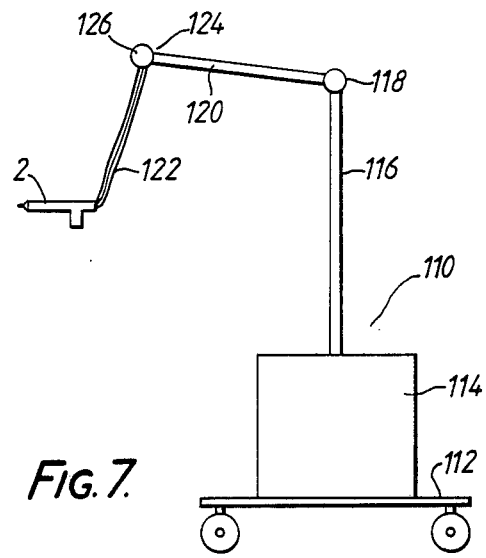
FIG. 7 is an elevational view of a mobile support for the apparatus shown in FIG. 1.

FIG. 7 shows a suspension device 110 for supporting the surgical aspirator 2 when it is being used in surgery. In many surgical operations in which the aspirator may be used, in particular in neurosurgery, the surgeon is required to hold the aspirator for a number of hours. The aspirator is fairly heavy and this can be a burden on the surgeon when he has to hold it for a period of time. Also, the power supply lines, irrigation lines and suction hose lines are connected to the aspirator and can get in the way of the surgeon. At present, an assistant is required to hold the lines and hose to ensure that they are kept away from the surgical field being operated upon.

The suspension device 110 includes a mobile base 112 on which is mounted a control box 114 which includes the controls and pumps for the aspirator 2. An upright member 116 extends upwardly from the base 112 and terminates at a positionable articulated joint 118 to which a cross member 120 is mounted. The joint 118 is a low friction joint which can be moved very smoothly but is also biased so that when the joint is set in a particular position it remains in that position until the cross member 120 is positively moved by the operator. The lines and hose 122 are fed along upright member 118 and cross member 120 and depend from the free end 124 of cross member 120. The free end 124 of the cross member 120 is provided with a device 126 for frictionally engaging the lines and hose 122. The engaging device 126 grips the lines and hose 122 and holds them so that the device 126 can support the weight of the surgical aspirator and the lines and hose 122 when they are allowed to hang freely from the cross member 120. The engaging device 126 permits the lines and hose 122 to be pulled smoothly and easily out of the cross member 120 with very little friction. Furthermore, those parts of the upright member 118 and the cross member 120 which contact the lines and hose 122 are coated with a low-friction material, such as teflon. The provision of the coating of low-friction material and the engaging device 126 permits the lines and hose 122 to be moved with very little friction into and out of the suspension device. The joint 118 and engaging device 126 ensure that the cross member and the surgical aspirator 2 do not move under their own weight but only when the surgical aspirator 2 and the lines and hose 122 are moved by the surgeon. This arrangement permits the weight of the aspirator 2 to be supported while allowing the aspirator 2 to be moved with very little frictional resistance. Thus, the aspirator 2 can be moved very small distances very smoothly. Also, the lines and hose 122 are fed from above and so are kept out of the surgeon's way.

While the present invention has been described in relation to an aspirator for use in surgery, the aspirator can also be used in other applications such as dentistry in which it can be used for drilling teeth. Such a dental drill would preferably employ a compressed gas-powered turbine as the motor for driving the vibrating tube.

What we claim is:

1. Apparatus for removing biological material from a body thereof comprising a hollow tubular elongate member, the tubular member having a cutting end which, in use, engages biological material to be removed, the cutting end having an annular cutting edge formed along the transverse end edge of the tubular elongate member, a casing in which a portion of the tubular member is mounted for longitudinal sliding movement, a motor which is connected to the casing and has a rotatable drive shaft, the rotatable drive shaft being disposed transversely relative to the tubular member, means for coupling the rotatable drive shaft to the tubular member so as longitudinally to vibrate the tubular member, the means for coupling engaging a middle portion of the tubular member, and means for withdrawing removed biologicial material through the tubular member from the said cutting end thereof, the means for withdrawing being located on a side of the means for coupling which is remote from the cutting end and comprising a chamber within the casing into which extends an end of the tubular member which is remote from the cutting end, and a port in the casing which communicates with the chamber and to which a suction tube can be attached.

2. Apparatus according to claim 1 further comprising means for supplying liquid to the cutting end of the tubular member.

3. Apparatus according to claim 1, wherein the means for coupling comprises a cam member which is mounted on the drive shaft and a cam follower which is mounted on the tubular member, the cam member engaging the cam follower.

4. Apparatus according to claim 3, wherein the cam member comprises a drive wheel which is eccentrically mounted on the drive shaft and bearing means for engaging the cam follower and coupling the drive wheel to the cam follower.

5. Apparatus according to claim 4, wherein the bearing means is an annular ball race which is mounted adjacent a transverse end face of the drive wheel about a lug which is mounted on and extends axially away from the said end face of the drive wheel, and wherein the cam follower is a body which has a channel therein in which the ball race is disposed and a cam surface of the cam member bears against opposing sides of the channel.

6. Apparatus according to claim 3, wherein the tubular member is removably fixed to the cam follower.

7. Apparatus according to claim 1, wherein at least a part of that portion of the tubular member which protrudes from the casing is flexible.

8. Apparatus according to claim 1, further comprising means for illuminating the cutting end of the tubular member.

9. Apparatus according to claim 8, wherein the means for illuminating includes a light guide which extends along the tubular member.

10. Apparatus according to claim 8, wherein the means for illuminating includes at least a part of the tubular member which is made of a light-transmissive material and acts as a light guide for directing light towards the cutting end of the tubular member.

11. Apparatus according to claim 1, wherein the motor is capable of vibrating the tubular member at a frequency of about 300 Hz.

12. Apparatus according to claim 11, wherein the motor is capable of rotating the rotatable drive shaft at a speed of about 20,000 revolutions per minute.

13. Apparatus according to claim 1, wherein the motor is capable of vibrating the tubular member with an amplitude of about 1 mm.

14. Apparatus for removing biological material according to claim 1 in combination with a support device therefor, the support device comprising at least two arms which are joined by an articulated joint, one arm being connected to a base and another arm being provided with means for holding at least one flexible conduit to which the said apparatus is connected, and guide means for guiding the at least one conduit along the at least two arms, the guide means being provided with a low-friction material so as to reduce the frictional resistance to relative sliding motion between the at least one conduit and the arms.

* * * * *